(12) United States Patent
Kuba et al.

(10) Patent No.: US 10,773,107 B2
(45) Date of Patent: Sep. 15, 2020

(54) HOSE DEVICE FOR A BREATHING APPARATUS

(71) Applicant: MSA EUROPE GMBH, Jona (CH)

(72) Inventors: Thomas Kuba, Wildau (DE); Wolfgang Weber, Berlin (DE)

(73) Assignee: MISA Europe GmbH, Jona (CH)

( * ) Notice: Subject to any disclaimer, the term of this patent is extended or adjusted under 35 U.S.C. 154(b) by 86 days.

(21) Appl. No.: 15/124,242

(22) PCT Filed: Mar. 31, 2015

(86) PCT No.: PCT/EP2015/057049
§ 371 (c)(1),
(2) Date: Sep. 7, 2016

(87) PCT Pub. No.: WO2015/150396
PCT Pub. Date: Oct. 8, 2015

(65) Prior Publication Data
US 2017/0173369 A1   Jun. 22, 2017

(30) Foreign Application Priority Data
Apr. 4, 2014   (DE) .................. 10 2014 206 508

(51) Int. Cl.
| | |
|---|---|
| *A62B 7/12* | (2006.01) |
| *A61M 16/08* | (2006.01) |
| *A62B 18/08* | (2006.01) |
| *A62B 9/00* | (2006.01) |
| *A62B 9/04* | (2006.01) |

(52) U.S. Cl.
CPC ........... *A62B 7/12* (2013.01); *A61M 16/0875* (2013.01); *A62B 9/006* (2013.01); *A62B 9/04* (2013.01); *A62B 18/08* (2013.01); *A61M 16/0858* (2014.02); *A61M 2205/3633* (2013.01)

(58) Field of Classification Search
CPC ... A62B 9/04; A62B 9/006; A62B 7/12; F16L 9/147; F16L 39/02; A61M 16/0875; A61M 16/0858; A61M 2205/3633
USPC ......... 285/151.1, 154.2, 222.1, 222.2, 222.3, 285/222.4, 222.5; 128/202.27, 200.24
See application file for complete search history.

(56) References Cited

U.S. PATENT DOCUMENTS

| | | | | |
|---|---|---|---|---|
| 4,265,235 | A * | 5/1981 | Fukunaga | 128/200.24 |
| 8,235,042 | B2 * | 8/2012 | Newman, Jr. | 128/200.24 X |
| 2003/0000530 | A1 | 1/2003 | McDonald et al. | |
| 2006/0232065 | A1 * | 10/2006 | Burke | 285/222.1 X |
| 2014/0203549 | A1 * | 7/2014 | Stednitz | |

FOREIGN PATENT DOCUMENTS

| | | |
|---|---|---|
| DE | 1227737 B | 10/1966 |
| DE | 29602060 U1 | 3/1996 |
| DE | 29601293 U1 | 4/1996 |
| DE | 19949283 A1 | 4/2001 |
| EP | 0574371 A1 | 12/1993 |

(Continued)

OTHER PUBLICATIONS

International Search Report for PCT/EP2015/057049, 3 pages.

*Primary Examiner* — Zachary T Dragicevich
(74) *Attorney, Agent, or Firm* — The Webb Law Firm

(57) ABSTRACT

An embodiment relates to a hose device for a breathing apparatus, characterized by at least one electric line (2) and at least one pressure line (3) within the open-cross-section of the hose device (1).

20 Claims, 2 Drawing Sheets

(56) References Cited

FOREIGN PATENT DOCUMENTS

| EP | 1127583 A2 | 8/2001 | |
|----|----|----|----|
| FR | 2845922 A1 | 4/2004 | |
| GB | 2463426 A | 3/2010 | |
| GB | 2485832 A | 5/2012 | |
| WO | WO-2014088430 A1 * | 6/2014 | ........ A61M 16/0875 |

* cited by examiner (A-A)

HOSE DEVICE FOR A BREATHING APPARATUS

CROSS REFERENCE TO RELATED APPLICATIONS

This application is the National Stage Application of International Application No. PCT/EP2015/057049, filed Mar. 31, 2015, which claims priority to German Patent Application Serial No. DE 10 2014 206 508.9 filed on Apr. 4, 2014 the content of both of which is incorporated by reference in its entirety herein.

TECHNICAL FIELD

The subject matter relates to an hose device for a breathing apparatus

When using breathing apparatuses, as used for example in fire departments, in mines or in industrial facilities, the safe functioning of the equipment is of great importance.

In modern breathing apparatuses, the certain equipment and parts used therein must be supplied with electrical energy, and data must be transported therefrom. In addition, pressure lines, in particular air pressure lines must also be fed between various parts of the breathing apparatus.

BRIEF SUMMARY

One embodiment provides a hose device for a breathing apparatus characterized by at least one electric line (2) and at least one pressure line (3) within the open cross-section of the hose device (1).

Another embodiment provides a hose device for a breathing apparatus, comprising: an area of the hose device having an open cross-section; at least one connecting part that connects to the breathing apparatus; at least one electric line within the open cross-section area; and at least one pressure line within the open cross-section area An further embodiment provides a hose device for a breathing apparatus, comprising: an area of the hose device having an open cross-section; at least one connecting part that connects to the breathing apparatus; at least one electric line within the open cross-section area; and at least one pressure line within the open cross-section area; wherein the at least one pressure line and is helically arranged about the at least one electric line within the open cross-section area.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

Embodiments of the present invention are described with reference to drawings, in which.

DETAILED DESCRIPTION

Figure 1:
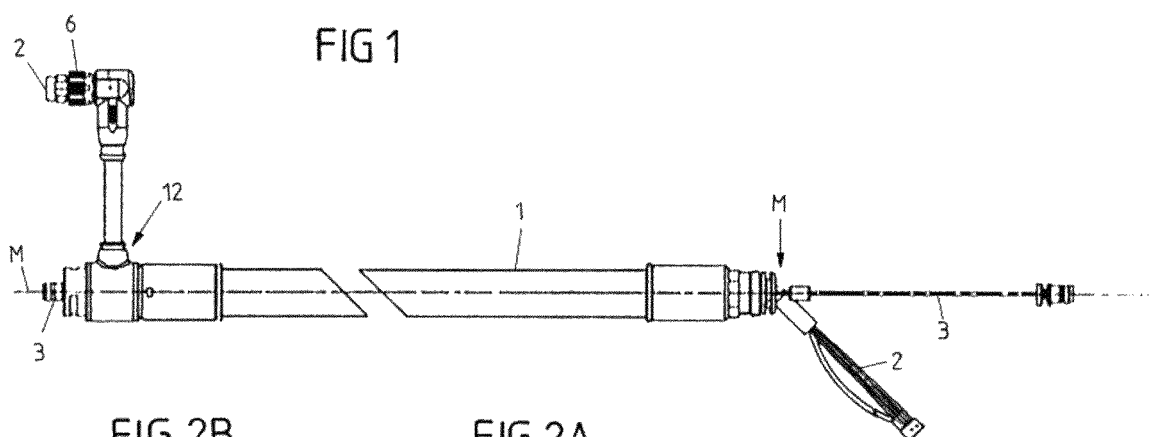
FIG. 1 shows an embodiment of a hose device having a pressure line and an electric line.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of certain example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of certain embodiments. One skilled in the relevant art will recognize, however, that the various embodiments can be practiced without one or more of the specific details, or with other methods, components, materials, etc. In other instances, well known structures, materials, or operations are not shown or described in detail to avoid obfuscation. The following description is intended only by way of example, and simply illustrates certain example embodiments.

In modern breathing apparatuses, the certain equipment and parts must be supplied with electrical energy and data must be transported therefrom. In addition, pressure lines must also be fed between various parts of the breathing apparatus.

An embodiment creates a secure connection for such pressure lines.

Arranged in the hose device is at least one electrical line and at least one pressure line within the open cross-section of a hose.

In one embodiment of the hose device at least one pressure line is designed as a high pressure line, in particular as a high pressure capillary tube for pressures from 20 to 500 bar, in particular between 200 and 400 bar. In this design, the high pressure line may be used to transmit pneumatic signals and/or supply air.

In addition to the at least one high pressure line, gas or a gas mixture may also be transported in an intermediate pressure line.

Pneumatic signals may be transmitted through the at least one pressure line, in particular through a high pressure capillary tube which is coupled to an analog manometer 13, a warning device 14, in particular an acoustic warning whistle, a pneumatic device and/or a pressure sensor.

Since hose devices are regularly moved when in use, it is useful for the at least one pressure line to be expandably arranged within the open cross-section of the hose device. In this arrangement the at least one pressure line may include expandable regions in the longitudinal direction which permit an expansion in the longitudinal direction, for example, at a flexure in the hose device.

By arranging the at least one pressure line, in particular the high pressure line, at least in sections helically around the at least one electric line, an improved expansion effect is achieved for one, and for another the electric line is protected by the pressure line wrapped around it.

In one embodiment the at least one pressure line is constructed at least partially of metal and/or plastic, in particular PTFE or another Fluorine substitutes plastic.

In this case, the hose line may include a sheathing having a wall made of plastic, in particular of rubber, and/or of silicone.

In another embodiment, the at least one electric line and the at least one pressure line at (at least) one end of the hose device exit in parallel and/or coaxially from the hose device. In addition or alternatively, the at least one electric line and the at least one pressure line at (at least) one end of the hose device may exit separately through the wall of the hose device. Which decoupling of the lines from the hose device is selected may depend on the units to which the hose device is to be connected. It is also possible in one embodiment to enclose the at least one electric line with a protective element in the region of feed out from the hose device. The protective element serves as a seal and/or as thermal protection. In this case, the protective element may be designed as an overmolded part or extrusion-coated part.

In another embodiment, the at least one electric line and/or at least one pressure line is enclosed by a sealing element in the region of one end of the hose.

In another configuration, the at least one electric line and/or the at least one pressure line includes a connection part at the outlet of the hose device 1 for connecting to other units.

FIG. 1 shows a hose device 1 as it is used in connection with breathing apparatuses. In the embodiment shown, an electric line 2 and a pressure line 3 are arranged in the open cross-section of the hose device 1. The electric line 2 and the pressure line 3 are enclosed by a wall of the hose device 1. In alternative embodiments, more than one electric line 2 or pressure line 3 may be arranged in each case within the hose device 1.

Here, the pressure line 3 is designed as a high pressure line 3, namely, as a high pressure capillary tube which is able to transmit pneumatic signals from compressed air cylinders to an analog manometer, the compressed air cylinder and the manometer not being shown here. The pressure range of the high pressure capillary tube 3 in this case may lie between 200 and 400 bar. The inside diameter of the high pressure capillary tube in this embodiment is 0.55 mm.

The hose device 1 is an electro-pneumatic assembly.

In alternative embodiments the gas or gas mixtures may also be transported at other pressures through the pressure line 3.

The electric line 2 is used, for example, for supplying power to power units, for signal transmission (for example, audio transmission) and/or for data transmission.

Figures 2A, 2B:
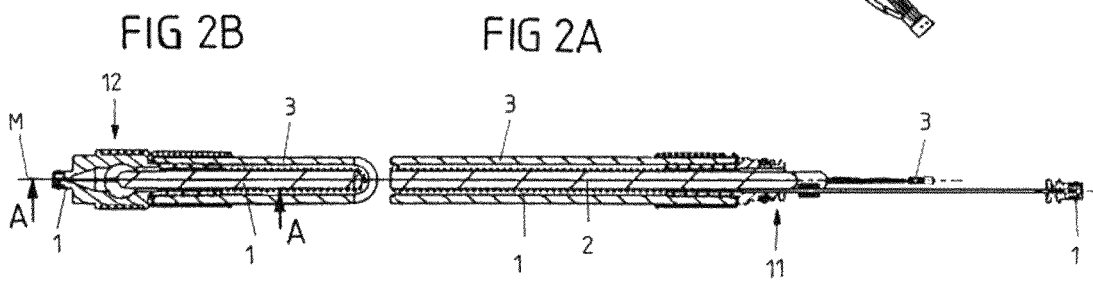
FIG. 2A shows a sectional view of a first end of the embodiment of the hose device according to FIG. 1.
FIG. 2B shows a sectional view of a second end of the embodiment of the hose device according to FIG. 2.

At a first end 11 of the hose device 1 the electric line 2 and the pressure line 3 are guided in parallel out of the hose device 1, which is shown in particular in FIG. 2A. Once the lines 2, 3 have left the outlet cross-section of the hose device 1, the lines 2, 3 may run in different directions; in the outlet cross-section they are arranged in parallel. Alternatively, the lines 2, 3 may also be coaxial in design.

At a second end 12 of the hose device 1 the electric line 2 and the pressure line 3 are separated at an angle in such a way that both lines 2, 3 are able to leave the hose 1 offset from one another.

In the embodiment shown (see also FIG. 3), the pressure line 3 leaves the hose device 1 essentially along a center axis M of the hose device 1. The electric line 2 is guided essentially at a right angle out of the hose device 1. A connecting piece of the electric line 2 is then aligned parallel to the center axis M.

FIG. 2A shows a sectional view through the hose device 1, at the first end 11 of which the parallel arrangement of the lines 2, 3 is apparent.

Situated approximately along the center axis M inside the hose 1, i.e. in the open cross-section of the hose device 1, is the electric line 2.

The pressure line 3, in this case a high pressure capillary tube, is made of metal and is helically arranged about the electric line 2. In this way, the hose device 1 with the lines 2, 3 situated therein may be flexed without placing the metal pressure line 3 under too much tensile stress. In addition to the wall of the hose device 1, the sheath formed by the helically designed pressure line 3 also offers a certain protection for the electric line 2.

In an alternative embodiment, the pressure line 3 is helically designed along only sections of the electric line 2. Each of these sections form expandable regions. Otherwise the pressure line runs straight along the electric line 2.

In another alternative embodiment, the expandable regions of the pressure line 3 may also be designed in such a way that some segments of the pressure line 3 may be bent into loops before the pressure line runs straight again. In this embodiment, the electric line 2 is not enclosed by the pressure line 3, since the otherwise straight-running high pressure line 3 extends along the surface of the electric line 2 and loops are situated in sections on the electric line 2.

FIG. 2B shows the second end 12 of the hose device 1 in a sectional view. Here too, the pressure line 3 exits essentially in the region of the center axis M. The ends of both the pressure line 3 as well as the electric line 2 are provided with connection elements 6 with which the lines 2, 3 may be attached to other units.

Figure 3:
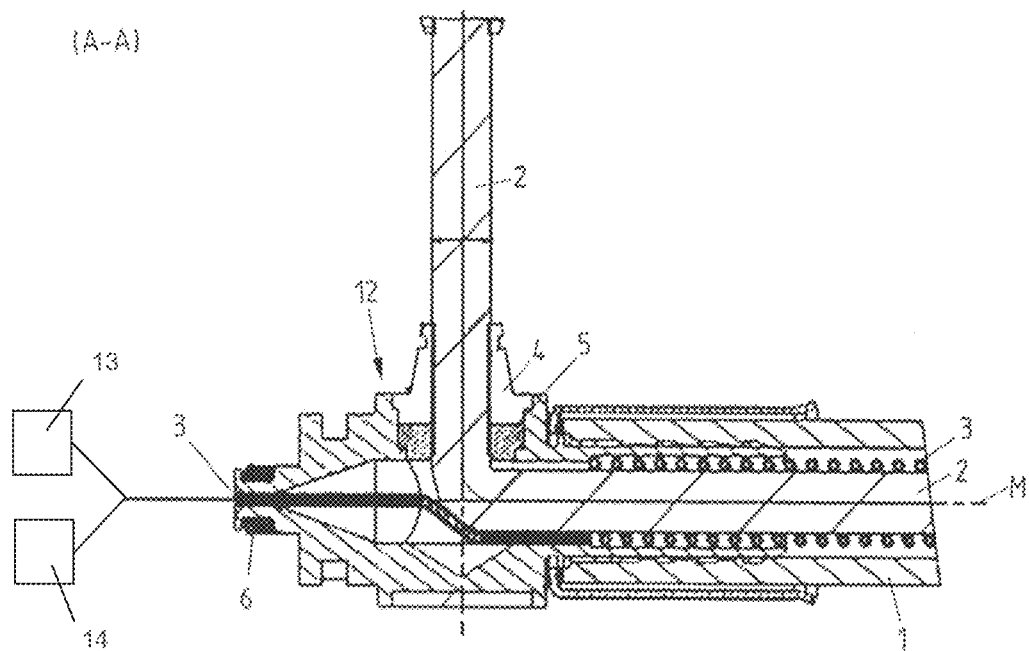
FIG. 3 shows another sectional view of the second end of the embodiment of the hose device according to FIG. 1.

The separation of the electric line 2 and the pressure line 3 at this point in the hose device 1 is also shown in the other sectional view in FIG. 3.

Here it is apparent that the pressure line 3, beyond the end of the helically wound portion, extends initially straight in parallel to the electric line 2. Once the electric line 2 is bent upward (essentially by 90°) out of the hose device 1, the pressure line 3 is guided into the region of the center axis M and then exits from the wall of the hose device 1.

At the outlet from the wall of the hose device 1, the electric line 2 is enclosed by a protective element 4 which in this case is designed as a casting or molding. Arranged below the protective element 4 is a sealing element 5 intended to block moisture. The connection of an overmolded protective element 4 having a sealing element 5 increases safety.

In an alternative embodiment, the pressure line 3 is guided out of one end 12 of the hose device 1 and the electric line 2 is guided essentially coaxially out of the end 12 of the hose device 1.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments of the invention have been described herein with reference to the accompanying drawings, it is to be understood that the embodiments of the invention are not limited to those precise embodiments, and that various other changes and modifications may be affected therein by one skilled in the art without departing from the scope or spirit of the disclosure.

LIST OF REFERENCE NUMERALS 1 hose device
2 electric line
3 high pressure line
4 protective element
5 sealing element
6 connection element
11 first end of the tube
12 second end of the tube

What is claimed is:

1. A hose device for a breathing apparatus, comprising:
an area of the hose device having an open cross-section;
at least one connecting part that connects to the breathing apparatus;
at least one electric line within the open cross-section area, the at least one electric line having a first longitudinal centerline extending along a longitudinal length of the at least one electric line; and
at least one hollow pressure line within the open cross-section area, the at least one hollow pressure line having a second longitudinal centerline extending along a longitudinal length of the at least one hollow pressure line,
wherein the second longitudinal centerline of the at least one hollow pressure line is arranged helically around at least a portion of the first longitudinal centerline of the at least one electric line, and
wherein a portion of the at least one electric line and a portion of the at least one hollow pressure line exit separately through at least one end of the hose device.

2. The hose device of claim 1, wherein the at least one pressure line is a high pressure capillary hose for pressures from about 20 to about 500 bar.

3. The hose device of claim 2, wherein the high pressure capillary hose has an internal diameter of about 0.55 mm.

4. The hose device of claim 1, wherein the at least one pressure line transmits pneumatic signals.

5. The hose device of claim 1, wherein the at least one pressure line transmits supply air.

6. The hose device of claim 1, wherein the at least one pressure line comprises at least one high pressure line.

7. The hose device of claim 1, wherein the at least one pressure line is coupled to an analog manometer and a warning device, the warning device being activated based on a predetermined pressure threshold.

8. The hose device of claim 1, wherein the at least one pressure line is expandable within the open cross-section area of the hose device.

9. The hose device of claim 1, wherein the at least one pressure line has regions expandable in a longitudinal direction.

10. The hose device of claim 1, wherein the at least one pressure line is constructed of a material selected from a group consisting of: a metal, and a plastic.

11. The hose device of claim 1, wherein the at least one pressure line is constructed of polytetrafluoroethylene.

12. The hose device of claim 1, wherein the at least one pressure line has a sheathing wall constructed of a material selected from a group consisting of: plastic, rubber, and silicone.

13. The hose device of claim 1, wherein the portion of the at least one electric line and the portion of the at least one pressure line are separated at an angle, in particular 90°, to each other when exiting the hose device.

14. The hose device of claim 13, wherein the at least one electric line enters a protective element at an exit of the hose device.

15. The hose device of claim 14, wherein a sealing element is located adjacent to the protective element.

16. The hose device of claim 14, wherein the protective element is an overmolded part.

17. The hose device of claim 14, wherein the at least one electric line and the at least one pressure line are enclosed in parallel in an exit situated in an end of the hose device.

18. The hose device of claim 1, wherein the first longitudinal centerline is non-parallel with the second longitudinal centerline in a region where the second longitudinal centerline is arranged helically around the first longitudinal centerline.

19. A hose device for a breathing apparatus, comprising:
an area of the hose device having an open cross-section;
at least one connecting part that connects to the breathing apparatus;
at least one electric line within the open cross-section area and configured for at least one of power supply, signal transmission, and data transmission, the at least one electric line having a first longitudinal centerline extending along a longitudinal length of the at least one electric line; and
at least one hollow pressure line within the open cross-section area and configured for at least one of transmitting a pressure signal and supplying air, the at least one hollow pressure line having a second longitudinal centerline extending along a longitudinal length of the at least one hollow pressure line;
wherein the second longitudinal centerline of the at least one hollow pressure line is helically arranged about at least a portion of the first longitudinal centerline of the at least one electric line within the open cross-section area, and
wherein a portion of the at least one electric line and a portion of the at least one hollow pressure line exit separately through at least one end of the hose device.

20. A hose device for a breathing apparatus, comprising:
an area of the hose device having an open cross-section;
at least one connecting part that connects to the breathing apparatus;
at least one electric line within the open cross-section area, the at least one electric line having a first longitudinal centerline extending along a longitudinal length of the at least one electric line; and
at least one hollow pressure line within the open cross-section area, the at least one hollow pressure line having a second longitudinal centerline extending along a longitudinal length of the at least one hollow pressure line,
wherein the second longitudinal centerline of the at least one hollow pressure line is arranged helically around at least a portion of the first longitudinal centerline of the at least one electric line, and wherein the at least one hollow pressure line is coupled to an analog manometer and a warning device, the warning device being activated based on a predetermined pressure threshold.

* * * * *

UNITED STATES PATENT AND TRADEMARK OFFICE
CERTIFICATE OF CORRECTION

Page 1 of 1

PATENT NO. : 10,773,107 B2
APPLICATION NO. : 15/124242
DATED : September 15, 2020
INVENTOR(S) : Thomas Kuba et al.

It is certified that error appears in the above-identified patent and that said Letters Patent is hereby corrected as shown below:

On the Title Page

Column 1, item (73) Assignee, Line 1, Delete "MISA" and insert -- MSA --

Column 2, item (57) Abstract, Line 3, Delete "open-cross-section" and insert -- open cross-section --

In the Specification

Column 1, Line 12, Delete "2014" and insert -- 2014, --

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*